United States Patent
Porter

(10) Patent No.: US 10,426,917 B2
(45) Date of Patent: Oct. 1, 2019

(54) SYSTEM AND METHOD FOR MANUFACTURING VARIABLE STIFFNESS CATHETERS

(71) Applicants: STRYKER CORPORATION, Kalamazoo, MI (US); STRYKER EUROPEAN HOLDINGS I, LLC, Kalamazoo, MI (US)

(72) Inventor: Stephen Porter, Piedmont, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 557 days.

(21) Appl. No.: 15/099,458

(22) Filed: Apr. 14, 2016

(65) Prior Publication Data

US 2016/0303347 A1    Oct. 20, 2016

Related U.S. Application Data

(60) Provisional application No. 62/148,335, filed on Apr. 16, 2015.

(51) Int. Cl.
*B29C 48/05* (2019.01)
*B29C 48/30* (2019.01)
(Continued)

(52) U.S. Cl.
CPC ........ *A61M 25/0012* (2013.01); *A61M 25/00* (2013.01); *B29C 48/0019* (2019.02);
(Continued)

(58) Field of Classification Search
CPC .......... A61M 25/0009; A61M 25/0012; A61M 25/0043; A61M 25/005; A61M 25/0053;
(Continued)

(56) References Cited

U.S. PATENT DOCUMENTS

| | | | |
|---|---|---|---|
| 3,787,265 A | 1/1974 | McGinnis et al. | |
| 4,540,360 A * | 9/1985 | Leo | B29C 53/12 425/384 |

(Continued)

FOREIGN PATENT DOCUMENTS

| | | |
|---|---|---|
| CN | 103921443 | 7/2014 |
| EP | 1432566 | 6/2004 |

(Continued)

OTHER PUBLICATIONS

PCT International Search Report and Written Opinion for International Application No. PCT/US2016/027601, Applicant Stryker Corporation, forms PCT/ISA/210, 220, and 237, dated Jul. 14, 2016 (14 pages).

(Continued)

*Primary Examiner* — Philip C Tucker
*Assistant Examiner* — Brian R Slawski
(74) *Attorney, Agent, or Firm* — Vista IP Law Group LLP

(57) ABSTRACT

A system for manufacturing a catheter includes at least first and second controllable rate material feeders that feed at least first and second materials into a temperature-controlled mixer to form a compound material that varies in flexibility and/or strength with the respective first and second materials and material feed rates. An extruder extrudes the compound material onto a rotating and translating mandrel to thereby form a variable stiffness profile along a length of the catheter that depends on respective rates of rotation and translation of the mandrel.

11 Claims, 7 Drawing Sheets

(51) Int. Cl.
| | |
|---|---|
| *B29C 48/92* | (2019.01) |
| *B29C 65/18* | (2006.01) |
| *B29C 65/00* | (2006.01) |
| *B32B 37/00* | (2006.01) |
| *A61M 25/00* | (2006.01) |
| *B29C 48/00* | (2019.01) |
| *B29C 48/157* | (2019.01) |
| *B29C 48/154* | (2019.01) |
| *B29C 48/285* | (2019.01) |
| *B29L 31/00* | (2006.01) |
| *B29C 53/56* | (2006.01) |
| *B29C 53/66* | (2006.01) |

(52) U.S. Cl.
CPC .......... *B29C 48/154* (2019.02); *B29C 48/157* (2019.02); *B29C 48/286* (2019.02); *B29C 48/2886* (2019.02); *B29C 48/92* (2019.02); *B29C 48/05* (2019.02); *B29C 48/30* (2019.02); *B29C 53/566* (2013.01); *B29C 53/66* (2013.01); *B29C 65/18* (2013.01); *B29C 66/69* (2013.01); *B29C 66/9141* (2013.01); *B29C 66/93411* (2013.01); *B29C 66/93451* (2013.01); *B29C 2948/926* (2019.02); *B29C 2948/9258* (2019.02); *B29C 2948/9259* (2019.02); *B29C 2948/92828* (2019.02); *B29C 2948/92876* (2019.02); *B29L 2031/7542* (2013.01)

(58) Field of Classification Search
CPC ........... A61M 25/0054; B29C 47/0014; B29C 47/0064; B29C 64/106; B29C 64/118; B29C 64/209; B29C 65/02; B29C 65/18; B29C 66/301; B29C 66/69; B29C 66/9141; B29C 66/934; B29C 66/93411; B29C 66/93451; B29C 48/05; B29C 48/30; B29C 48/304; B29C 48/345; B29C 48/92
USPC ... 156/60, 64, 150, 166, 167, 169, 172, 173, 156/175, 180, 181, 242, 244.11, 244.12, 156/244.13, 308.2, 309.6, 349, 350, 356, 156/359, 367, 378, 391, 392, 425, 428, 156/429, 430, 431, 432, 443, 446, 448, 156/500
See application file for complete search history.

(56) References Cited

U.S. PATENT DOCUMENTS

| | | | |
|---|---|---|---|
| 4,692,975 A * | 9/1987 | Garcia ................ | B05C 17/0207 492/29 |
| 4,767,400 A | 8/1988 | Miller et al. | |
| 5,003,918 A * | 4/1991 | Olson .............. | A61B 17/32075 118/416 |
| 5,121,329 A | 6/1992 | Crump | |
| 5,485,665 A * | 1/1996 | Marks ..................... | B65H 81/06 242/413.1 |
| 5,653,747 A | 8/1997 | Dereume | |
| 5,725,814 A * | 3/1998 | Harris ................. | B29C 47/0023 264/167 |
| 6,129,872 A | 10/2000 | Jang | |
| 6,192,958 B1 * | 2/2001 | Yamamoto ............. | A63B 53/10 156/432 |
| 6,627,127 B1 * | 9/2003 | Piovoso .................. | B29C 47/92 264/40.4 |
| 6,669,886 B1 | 12/2003 | Willard | |
| 6,923,634 B2 | 8/2005 | Swanson et al. | |
| 6,998,087 B1 | 2/2006 | Hanson et al. | |
| 7,604,470 B2 | 10/2009 | LaBossiere et al. | |
| 7,648,664 B2 | 1/2010 | Teal et al. | |
| 8,221,669 B2 | 7/2012 | Batchelder et al. | |
| 8,883,392 B2 | 11/2014 | Napadensky et al. | |
| 2007/0106361 A1 | 5/2007 | Epstein | |
| 2010/0260923 A1 | 10/2010 | Pursley | |
| 2010/0327479 A1 | 12/2010 | Zinniel et al. | |
| 2011/0079936 A1 | 4/2011 | Oxman | |
| 2011/0264235 A1 | 10/2011 | Chen et al. | |
| 2012/0135171 A1 * | 5/2012 | Swenson ............. | B29C 45/0053 428/35.7 |
| 2013/0123752 A1 * | 5/2013 | Pursley ............. | A61M 25/0009 604/528 |
| 2014/0134334 A1 | 5/2014 | Pridoehl et al. | |
| 2014/0242208 A1 | 8/2014 | Elsworthy | |
| 2014/0265034 A1 | 9/2014 | Dudley | |
| 2014/0284838 A1 | 9/2014 | Pfeffer et al. | |
| 2014/0324204 A1 | 10/2014 | Vidimce et al. | |

FOREIGN PATENT DOCUMENTS

| | | |
|---|---|---|
| KR | 101430582 B1 | 8/2014 |
| WO | 98/07523 | 2/1998 |
| WO | 2013/056023 | 4/2013 |

OTHER PUBLICATIONS

Orr, Tiffany, "3D Printed Models used to develop Smart Cardiac Catheters by EU Researchers and Materialise," at 3D Print.com, Jul. 9, 2014, accessed from: http://3dprint.com/8640/smart-catheters-3d-print.

Kadvany, Elena, "At Stanford, 3-D printing breaks new ground," at Palo Alto Weekly, Palo Alto online, Jul. 8, 2013, accessed from: http://www.paloaltoonline.com/news/2013/07/07/at-stanford-3-d-printing-breaks-new-ground.

* cited by examiner

SYSTEM AND METHOD FOR MANUFACTURING VARIABLE STIFFNESS CATHETERS

RELATED APPLICATION DATA

The present application claims the benefit under 35 U.S.C. § 119 to U.S. provisional patent application Ser. No. 62/148,335, filed Apr. 16, 2015. The foregoing application is hereby incorporated by reference into the present application in its entirety.

FIELD OF THE INVENTION

The present disclosure relates generally to medical devices such as intravascular catheters. More particularly, the present disclosure pertains to systems and methods of manufacturing variable stiffness catheters.

BACKGROUND

Intravascular catheters are used in a wide variety of minimally invasive medical procedures. Several types of catheters are utilized for intravascular treatment. Examples of intravascular catheters include guide catheters, angioplasty catheters, stent delivery devices, angiography catheters, neuro-catheters, and the like. Such intravascular catheters may be used for diagnostic or therapeutic purposes. Generally, an intravascular catheter enables a physician to remotely perform a medical procedure by inserting the catheter into the vascular system of a patient at a location that is easily accessible and thereafter navigating the catheter to the desired target site. Using such procedures, virtually any target site in the patient's vascular system may be remotely accessed, including the coronary, cerebral, and peripheral vasculature.

In order to function efficiently, many intravascular catheters require a relatively stiff main body portion and soft distal portion and tip. The stiff main body portion gives the intravascular catheter sufficient "pushability" and "torqueability" to allow it to be inserted, moved and rotated in the vasculature to position the distal end of the catheter at the desired site adjacent to a particular vessel. However, the distal portion should have sufficient flexibility so that it can track over a guidewire and be maneuvered through a tortuous path to the treatment site. In addition, a soft distal tip at the very distal end of the catheter should be used to minimize the risk of causing trauma to a blood vessel while the intravascular catheter is being moved through the vasculature to the proper position. Thus, variable stiffness catheters, having a relatively stiff proximal portion and a relatively flexible distal portion are desirable. Variable stiffness catheters are achieved by varying the properties of the materials used to manufacture the catheters.

One difficulty which has arisen for meeting demands for greater neurovascular catheter length is that the diameter of the distal section necessarily becomes smaller, since the longer catheters must reach ever narrower vascular areas. This smaller distal portion diameter requires a concomitant thinning of the wall section of the more distal portions of the catheter. The thinner distal section walls are able to attain even higher flexibility, which is a desirable trait because of the higher level of tortuosity in distal vasculature. In known methods of manufacturing catheters, those thinner walls have lower column strength and are more prone to kinking or rippling when actively pushed along the guidewire or when vaso-occlusive devices are pushed through the catheter's lumen. Furthermore, the different stiffness sections are matted creating joints which may not be sufficiently robust, or they may overlap and/or have sharp transition areas between the sections, which can increase susceptibility to kinking.

One known method of manufacturing catheters intended for use as angiography catheters or as guiding catheters often comprise a tubular liner surrounded by an outer tubular shell, with a reinforcing layer interposed there between. Either the outer shell or the liner, or both tubular elements may include relatively softer polymeric materials in a distal region of the catheter. Optionally, the reinforcing layer (e.g., tubular braid) may also have a more flexible, modified form in the distal region.

Another known method of manufacturing variable stiffness catheters is to produce a laminated catheter assembly with a uniform polymeric material. Selected regions of the catheter are then modified by radiation treatment to selectively increase stiffness. However, having a composite construction of a catheter using different materials is preferable and with this method of manufacturing, the choice of materials, as well as having control of the final catheter properties, is limited.

Another known method of manufacturing variable stiffness catheters requires sliding a series of tubular segments having different stiffness over (and onto) an inner assembly comprising a liner surrounded by a reinforcing layer. The tubular segments are shrink-fitted and melt-bonded to the inner assembly using a removable length of heat-shrink tubing. Such a process is labor intensive and inefficient since it requires many different materials for each segment and the catheters can only be fabricated one-at-a-time.

Yet another method of manufacturing catheters requires a continuous extrusion of a first rigid polymer to form an inner tubular body. Then, extruding a second soft, pliable polymer over (onto) the rigid tubular body to form an outer layer. Additionally, the catheter may be reinforced with a stiffening material, typically a wire cord or a braid wrapped around or embedded within the layers of the catheter. However, the distal section of the catheter may not be soft enough or the proximal section may not be stiff enough by limiting the materials to just one type of inner rigid layer and one type of soft pliable polymer, making this type of catheter unsuitable for passage through tortuous vasculature.

In another manufacturing method known as reel-to-reel process, an outer jacket material is varied by switching between extrusion sources as a continuous length of inner assembly passes through a wire-coating type extruder head. Alternatively, discrete sections of one material are extruded or over-molded onto the continuous length of inner assembly. A different material is then extruded onto the length of inner assembly, filling in the spaces between the discrete sections. After forming the continuous, variable stiffness outer shell, the long assembly is cut into catheter length sections. Although, the reel-to-reel method is a more cost efficient than assembling catheters one-at-a-time, the use of different materials to achieve variable catheter stiffness requires multiple assembly steps and/or complex tooling, and the junctions between the different material sections require careful control of design and manufacturing to avoid potentially weak joints that could fail during use.

Another method of manufacturing variable stiffness catheters include cutting segments of multi-layer tubular members and joining them together end to end, with the distal segment having a reduced durometer and/or thickness compared to its adjacent more proximal segment. However, the joints created by the mating of segments of tubular members may not be sufficiently robust to sustain tensile strength and other reliability requirements. This is because most of the tubular members for catheters are multi-layers extrusions having an innermost layer made of polytetrafluoroethylene (PTFE) that is particularly difficult to join end-to-end and is typically not melt-bond compatible with a nylon or polyether block amide (Pebax®) outermost layer. Butt-join or lap-join multi-layer tubular member segments have been unreliable because all abutting or overlapping layers tend not to successfully bond to one another.

Further approaches to improve joint reliability and overall manufacturability have common drawbacks, such as the tubing needed to be heated along its entire length to bond the various pieces together, and an entire length of shrink tubing covering the length of the tubing must be used to bond the layers and then discarded. Depending on the length of the variable stiffness catheter, the extended shrink tubing amounts to a considerable overall cost increase (multiple extrusions, shrink tubing, more direct labor required for assembly) relative to a conventional multi-layer extrusion, making the cost essentially prohibitive for highly segmented variable stiffness catheters.

The above described methods of manufacturing, particularly, the current fused extrusion methods are laborious and time intensive. Significant amounts of hand work and reliance on long lead items such as extruded tubing makes the process of design iteration time consuming and skill dependent. In addition, the current methods of manufacturing lack some design flexibility, especially in the area of material stiffness transitions. Thus, more graded transitions are desirable but are not used in complex designs requiring complex transitions. Furthermore, in many cases there is a need to have an inner and outer layer of a catheter shaft made of different materials, and although, this can be achieved with co-extruded tubing or multiple layers of laminated tubing, the design flexibility is limited in view of required specialized tubing builds and long lead times.

SUMMARY

In an exemplary embodiment of the disclosed inventions, a system for manufacturing a variable stiffness catheter includes a first material feeder coupled to a first material source; a second material feeder coupled to a second material source; and a thermally controlled mixer coupled to the first and second material feeders, wherein the first material feeder is configured to feed a first material from the first material source into the mixer at a first material feed rate, and the second material feeder is configured to feed a second material from the second material source into the mixer at a second material feed rate, such that the first and second materials are combined in the mixer to form a compound material that varies in content as a function of the respective first and second materials, and of the first and second material feed rates. The system further includes a catheter formation mandrel having a longitudinal axis, the mandrel being controllably rotatable about the longitudinal axis at mandrel rotation rate. An extruder is operatively coupled to the mixer and having an output nozzle configured to apply compound material from the mixer onto the catheter formation mandrel. A control system is provided, including one or more processors that control one or more of the first material feed rate, second material feed rate, and mandrel rotation rate, respectively, so as to enable formation of a catheter having a variable stiffness profile along a length of the catheter. The first and second materials preferably have different elasticity and/or strength characteristics, wherein an elasticity and/or strength of the compound material may be varied by controlling one or both of the first and second material feed rates.

The mixer may include a heated mixing chamber, where the control system controls a temperature of the mixing chamber. In such embodiments, the extruder may apply the compound material onto the catheter formation mandrel at a material extrusion rate controlled by the control system independently of the respective first and second material feed rates.

In various embodiments, the extruder and/or extruder nozzle being translatable along the longitudinal axis of the catheter formation mandrel at an extruder translation rate controlled by the control system. In such embodiments, the control system may vary the wall thickness along a length of at least a portion of a catheter being formed on the mandrel by varying one or more of the first material feed rate, second material feed rate, mandrel rotation rate, and extruder translation rate. By way of non-limiting example, the control system may adjust one or more of the first material feed rate, second material feed rate, mandrel rotation rate, and extruder translation rate based on real-time measurement data of a diameter of a portion of a catheter being formed on the mandrel.

In various embodiments, one or more heating elements are disposed adjacent or otherwise in proximity to a location at which the extruder applies the compound material onto the mandrel. By way of non-limiting example, a first heating element may be disposed on a first side of the mandrel adjacent or otherwise in proximity to a location at which the extruder applies the compound material onto the mandrel, and a second heating element may be disposed on an opposing side of the mandrel from the first heating element. In such embodiments, the one or more heating elements may be coupled to, so as to translate along the mandrel with, the extruder and/or extruder nozzle.

The system may further include a third material feeder coupled to a third material source, wherein the third material feeder is configured to feed a third material from the third material source into the mixer at a third material feed rate controlled by the system controller, such that the first, second and third materials are combined in the mixer to form the compound material, and wherein the compound material varies in content as a function of the respective first, second and third materials, and of the first, second and third material feed rates. Additional material feeders may also be employed.

In accordance with another aspect of the disclosed inventions, a method for manufacturing a variable stiffness catheter includes feeding a first material into a thermally controlled mixer at a first material feed rate; feeding a second material into the thermally controlled mixer at a second material feed rate, such that the first and second materials are combined in the mixing chamber to form a compound material that varies in content as a function of the respective first and second materials and first and second material feed rates; extruding the compound material from the mixer onto a catheter formation mandrel while rotating the mandrel about a longitudinal axis thereof at a mandrel rate of rotation; and controlling one or more of the first material feed rate, second material feed rate, and mandrel rotation rate, respectively, so as to form a catheter on the mandrel, the catheter having a variable stiffness profile along a length thereof. The first and second materials preferably have different elasticity and/or strength characteristics, and the method may further include adjusting one or both of the first and second material feed rates to vary an elasticity and/or strength of the extruded compound material.

In some embodiments, the mixer has a heated mixing chamber, and the method includes controlling a temperature of the mixing chamber. In such embodiments, extruding the compound material onto the catheter formation mandrel specifically includes extruding the compound material onto the mandrel at a material extrusion rate that is controlled independently of the respective first and second material feed rates.

An extruder having an extruder nozzle may be used for extruding the compound material from the mixer onto the catheter formation mandrel, and the method may further include translating the extruder and/or extruder nozzle along the longitudinal axis of the catheter formation mandrel at a controlled extruder translation rate. In particular, the method may include adjusting one or more of the first material feed rate, second material feed rate, mandrel rotation rate, and extruder translation rate in order to vary a wall thickness along a length of at least a portion of a catheter being formed on the mandrel. By way of non-limiting example, the method may include adjusting one or more of the first material feed rate, second material feed rate, mandrel rotation rate, and extruder translation rate based on real-time measurement data of a diameter of a portion of a catheter being formed on the mandrel.

In various embodiments, the method includes applying heat to the extruded material on the mandrel at one or more locations adjacent or otherwise in proximity to a location at which the compound material is extruded onto the mandrel. In one such embodiment, the method includes applying heat using a first heating element disposed on a first side of the mandrel adjacent or otherwise in proximity to a location at which the compound material is extruded onto the mandrel, and applying heat using a second heating element disposed on an opposing side of the mandrel from the first heating element. The first and second heating elements may be are coupled to, so as to translate along the mandrel with, the extruder and/or extruder nozzle.

The method may further include feeding a third material into the thermally controlled mixer at a third material feed rate, such that the first, second and third materials are combined in the mixer to form the compound material, and wherein the compound material varies in content as a function of the respective first, second and third materials, and of the first, second and third material feed rates.

Other and further aspects and features of embodiments of the disclosed inventions will become apparent from the ensuing detailed description in view of the accompanying figures.

DETAILED DESCRIPTION OF THE ILLUSTRATED EMBODIMENTS

Figure 1:
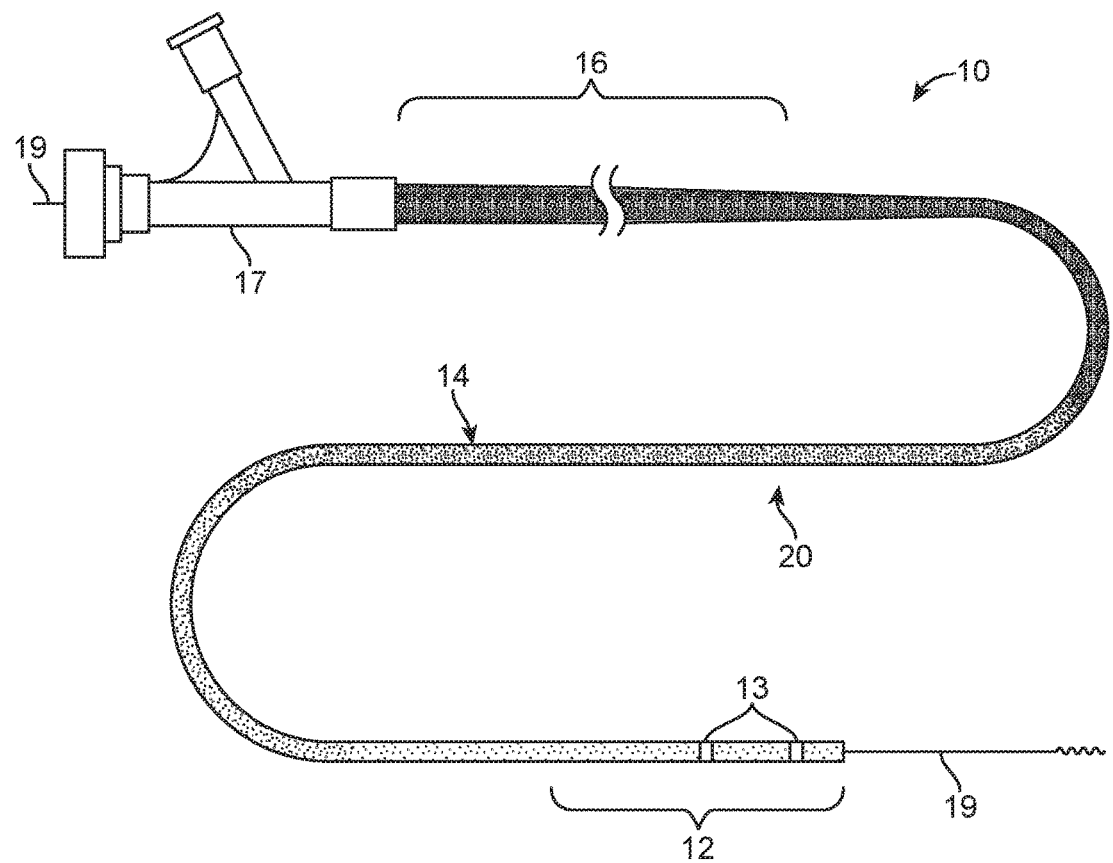
FIG. 1 is a side view of a variably stiffness catheter according to embodiments of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

An exemplary neurovascular multi-section catheter 10, manufactured in accordance with the disclosed embodiments, is depicted in FIG. 1. The design of the catheter 10 is particularly suitable for neurological and peripheral vascular applications, but is also suitable for less demanding applications, such as (without limitation) access and treatment of the heart. In particular, the presently disclosed methods of catheter manufacturing (described below in greater detail) are directed to formation of a tubular member 20 used to form the elongate body portion of catheter 10, wherein the tubular member 20 has gradual stiffness transitions and higher kink resistance than traditionally manufactured catheters. Because extruded materials have anisotropic strength properties, the material is typical stronger in the direction of the axis of extrusion than in any other orthogonal directions due to polymer chain orientation that develops as the material is drawn and cooled.

In an exemplary embodiment, the tubular member 20 is manufactured in a circumferential orientation by extruding compound material (mixture of plurality of materials at desirable rates) in a coil-like configuration; making the tubular member 20 more kink resistant as the higher strength direction is circumferential and adapted to maintain a substantially circular wall configuration (e.g., cross-section, lumen) while the tubular member is subject to bending forces. Thus, the tubular member 20 is believed to have superior performance when navigating the neuro-vasculature, as opposed to traditionally made catheters made in a linear orientation, in which the higher strength direction is longitudinal, resulting in a tendency to form an oval wall configuration (e.g., cross-section, lumen) when the catheter is subject to bending.

The catheter 10 depicted in FIG. 1 has a distal section 12 having significant flexibility, an intermediate section 14 which is typically less flexible than the distal section 12, and a long proximal section 16 which in turn is least flexible. The distal section 12 is flexible and soft to allow deep penetration of the extraordinary convolutions of the neurological vasculature without trauma. Usually, the typical dimensions of neurovascular catheters are: overall length: 125-200 cm; proximal section 16: 50-150 cm; intermediate section 14: 5-100 cm; and distal section 12: 2-30 cm. It should be appreciated that these dimensions are only guidelines, and are selected as a function of the malady treated and its site within the body.

Although the proximal 16, intermediate 14, and distal 12 sections of the catheter 10 may be considered as distinct sections, the transition between these sections may be smooth and substantially gradual (as depicted in FIG. 1 by the color degradation in catheter 10), such as, the variation in stiffness from the least flexible to the more flexible section is in a substantially continuous gradient in the disclosed inventions. Various accessories to the catheter assembly have been added, e.g., one or more radiopaque marker bands 13 at the distal region 12 to allow viewing of the position of the distal region under fluoroscopy, and a Luer assembly 17 for guidewire 19 and fluids access, are also shown in FIG. 1.

Figure 2:
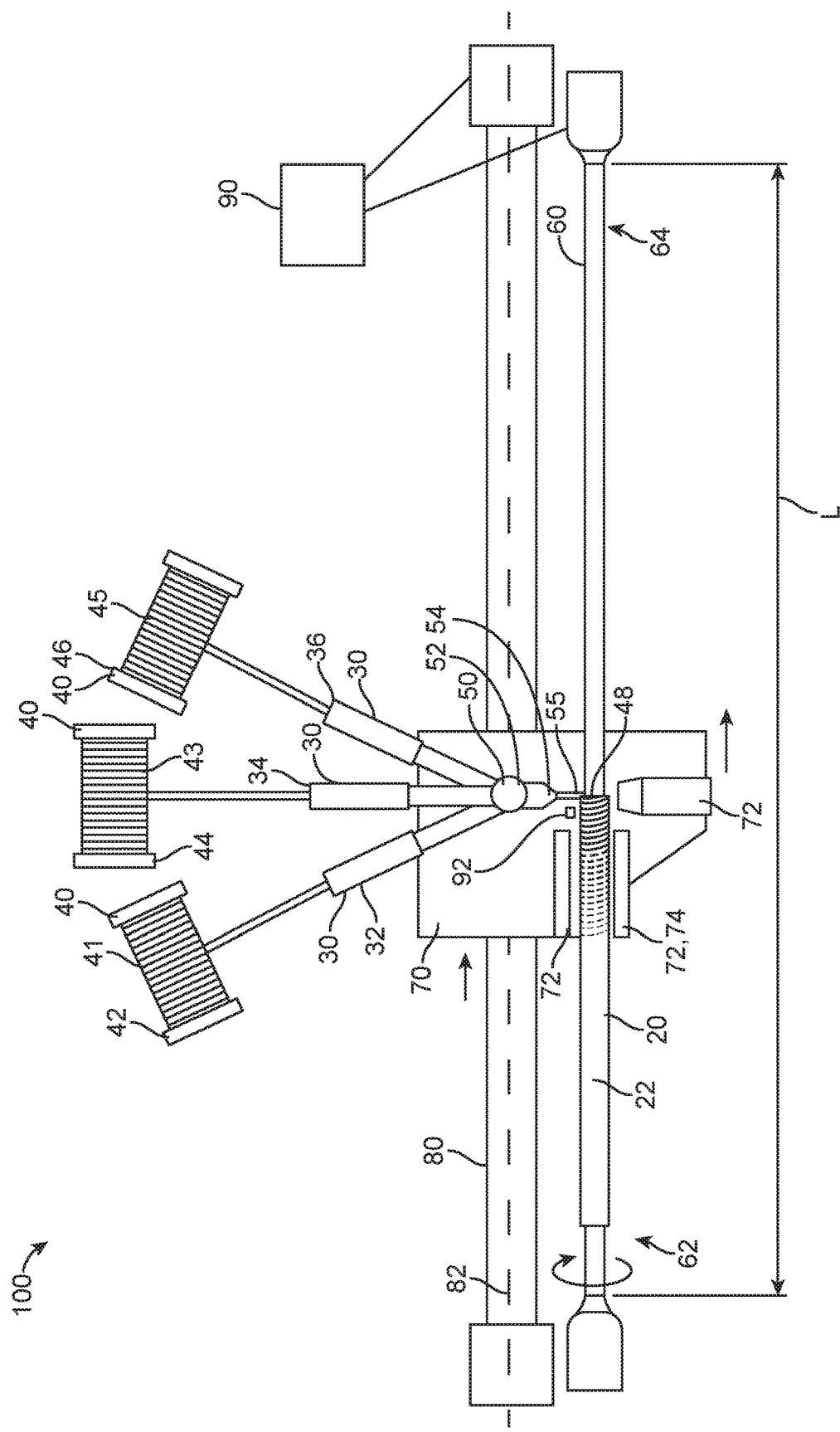
FIG. 2 is a side view of a variable stiffness catheter manufacturing assembly according to one embodiment of the disclosed inventions.

FIG. 2 is a side view of an exemplary catheter manufacturing assembly 100 provided for producing a variable stiffness elongate tubular member 20 (i.e., catheter), in accordance with embodiments of the disclosed inventions. The manufacturing assembly 100 includes a plurality of actuators 30 configured to feed a plurality of suitable polymeric materials 40 into a thermally controlled mixer 50. The mixer 50 preferably includes a heating chamber 52, wherein the plurality of materials 40 are heated to form a blended compound material 48 for delivery through an extruder comprising thermoplastic extrusion nozzle 55 onto a catheter formation mandrel 60. Additionally, the mixer 50 may include a mixing element 54 to assist on the formation of the compound material 48. The mixer 50 is mounted on a housing 70 that is slidable coupled to an elongated carrier 80; the carrier 80 allows translation or linear advancement of the housing 70 along a longitudinal axis 82 of the carrier 80. The carrier 80 may be disposed substantially parallel to the catheter formation mandrel 60.

The plurality of materials 40 may include polymeric filaments 41, 43 and 45 that are held in a plurality of cartridges 42, 44 and 46, respectively, and where each of the cartridges holds a material having different properties, such as, shore harness, elasticity, density, melting point, tensile strength or the like, or combinations thereof. It should be appreciated that the plurality of materials 40 comprises two or more materials, and more generally, that various suitable materials (e.g., biocompatible polymers, or the like), materials configuration (e.g., filaments, granulates, fluid, or the like), and material carriers (e.g., cartridges, bags, containers, or their like) or combinations thereof may be used in the manufacturing process. By way of non-limiting examples, the materials 40 may include polyether block amide (Pebax®) and Nylon. Other suitable materials that may be contemplated for making the assembly 100 include homopolymers, copolymers or polymer blends containing polyamides, polyurethanes, silicones, polyolefins (e.g., polypropylenes, polyethylenes), fluoropolymers (e.g., FEP, TFE, PTFE, ETFE), polycarbonates, polyethers, PEEK, PVC, and other polymer resins known for use in the manufacture of catheters.

By way of example, the filament 41 is composed of Pebax® 63D, the filament 43 is composed of Nylon 12, and the filament 45 composed of Pebax® 25D. Each of the filaments 41, 43 and 45, held in their respective cartridges 42, 44 and 46, are moved by their respective actuators 32, 34 and 36, and fed into the mixer 50 and heating chamber 52, respectively, where they are heated and melted to form the compound material 48. The plurality of materials 40 (i.e., filaments 41, 43 and 45) are mixed in the heating chamber 52 of the mixer 50 and melting process; and may be further mixed with the assistance of the mixing element 54. The ratio of materials 40 (i.e., 41, 43 and 45) in the compound material 48 is dynamically varied by a control system (or "unit") 90 comprising one or more processors coupled to the actuators 30, which controls the amount of material each actuator 32, 34 and 36 feeds into the mixer 50.

It should be appreciated that the compound material 48 will have different elasticity and strength depending on the ratio of each of the materials, (i.e., filament 41, 43 and 45) mixed in said compound. When a more elastic and softer compound material 48 is desired, the ratio of the more elastic and softer materials are increased and fed into the mixer 50, relative to the ratio of the less elastic or harder materials; for example, 1-49% of filament 41, 1-49% of filament 43 and 50-99% of filament 45. Conversely, when a less elastic and harder compound material 48 is desired, the ratio of the less elastic or harder materials are increased and fed into the mixer 50, relative to the ratio of the more elastic or softer materials; for example, 1-49% of filament 41, 50-99% of filament 43 and 1-49% of filament 45. The ratio of the materials fed into the mixer 50 may be varied in such a way that the composition of the compound material 48 varies in a substantially continuous gradient.

The compound material 48 is extruded out the extrusion nozzle 55 onto the catheter formation mandrel 60 to form the tubular member 20. The extrusion nozzle 55 has an opening 57 that allows the compound material 48 to be delivered onto the catheter formation mandrel 60. By way of example, the opening 57 can have a variety of shapes including but not limited to: a circular (FIG. 4B), elliptical (FIG. 4C), rectangular (not shown), or the like, adapted to extrude the compound material 48. The extrusion rate of the compound material 48 from the nozzle 55 on the mandrel 60 is substantially constant, for example, in a range between about 0.05 inches per second to about 10 inches per second. The extrusion rate is controlled by one or more processors of the control unit 90, and may be varied depending on variable factors, described in further detailed below.

Alternatively, one (or more) of the filaments 41, 43 or 45 of the plurality of materials 40 may be composed of a material having a higher melting point than the previously described polymeric materials, such as, metal or metal alloy (e.g., stainless steel, Nitinol, CoCr alloys, platinum and Pt alloys, tantalum and Ta alloys), aramid, carbon fiber, liquid crystalline polymers (e.g., Vectran), ceramic or the like of combination thereof, and adapted to be co-extruded with the compound material 48 composed by the remaining polymeric filaments, in order to provide additional structural support to the tubular member 20 when the compound material 48 is extruded thereon. By way of example, a metallic filament 41 may be co-extruded out (or alongside of) the nozzle 55 simultaneously with a compound material 48 formed by polymeric filaments 43 and 45 onto the catheter formation mandrel 60 to form the tubular member 20. For clarity, it should be understood that the reinforcing metallic filament 41 may pass-through or bypass the respective heating camber 52 and/or mixer 50, and my pass-through or bypass the nozzle 55. When co-extruded in this manner, the filament 41 forms a core having a polymeric coating provided by the compound material 48.

Figure 4B:
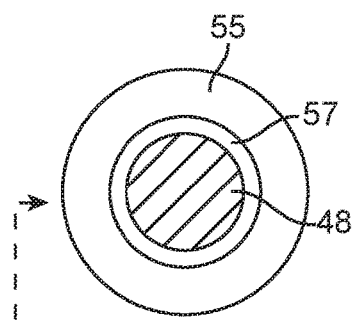
FIGS. 4A-C are side and cross-sectional views of the extrusion interface of the catheter manufacturing assemblies of FIGS. 2-3.
Figure 4A:
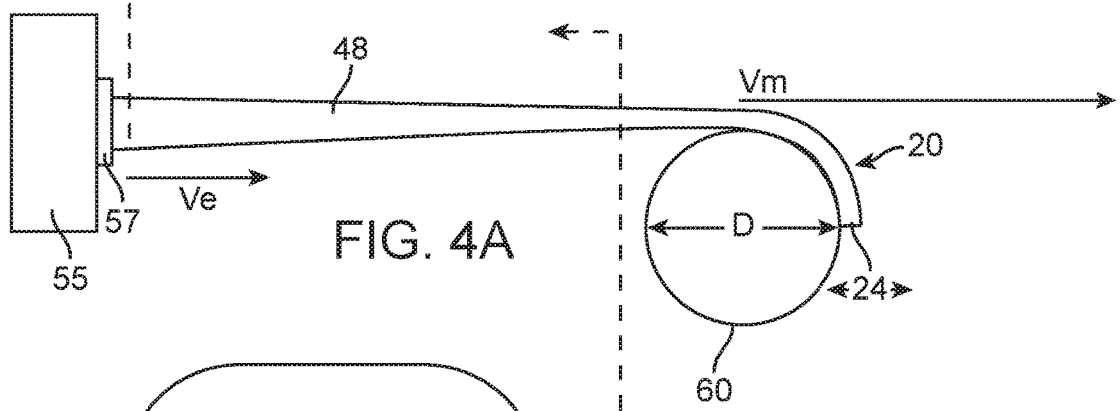
Figure 5A:
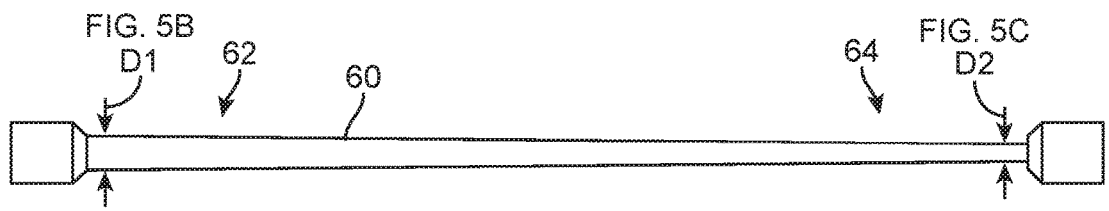
FIGS. 5A-C are side and cross-sectional views of a rotational mandrel according to an embodiment of the disclosed inventions.
Figure 5B:
Figure 5C:

The catheter formation mandrel 60 has an elongate configuration having a proximal portion 62, a distal portion 64 and a substantially circular cross-section having a diameter D (FIG. 4A). The diameter D is substantially constant along a length L of the catheter formation mandrel 60 (FIG. 1). The typical diameter D of the mandrel 60 is in a range of about 0.010 in to about 0.100 in. It should be appreciated that the catheter formation mandrel 60 may have an alternative shape, such as conical, tapered or other suitable configurations. For example, the catheter formation mandrel 60 of FIG. 5A is tapered having a diameter D1 in the proximal portion 62 (FIG. 5B) that is greater than a diameter D2 in the distal portion 64 (FIG. 5C). The typical diameter D1 is in a range of about 0.012 in to about 0.10 in, and the typical diameter D2 is in a range of about 0.008 in to about 0.090 in. The catheter formation mandrel 60 is preferably operatively coupled with a motor or equivalent means controlled by the control unit 90 for rotating the mandrel 60 about and along a longitudinal axis of the mandrel 60. The rotational speed (or "rate") in revolutions per unit of time of the catheter formation mandrel 60 may be varied during the catheter manufacturing process, depending on design factors, as described below in further detail.

In the embodiment of FIG. 2, the catheter formation mandrel 60 is disposed substantially parallel to the elongate carrier 80 that allows translation of the housing 70, including translation of the respective mixer 50 and extrusion nozzle 55, coupled to the housing 70. While the extrusion nozzle 55 extrudes the compound material 48 on the catheter formation mandrel 60, the nozzle 55 moves along with the housing 70 that translates along the longitudinal axis 82 of the carrier 80, and the mandrel 60 rotates simultaneously thereby forming the tubular member 20. The thickness of the extruded compound material 48, and therefore the thickness of the tubular member 20, depends on a variety of factors, such as (without limitation), the extrusion rate or speed of the extruded compound material 48 out of the nozzle 55, the rotational rate or speed of the catheter formation mandrel 60, the translation rate (i.e., linear distance per unit of time) of the nozzle 55, and the diameter of the mandrel 60. In an alternatively embodiment, the catheter formation mandrel 60 may be configured to linearly translate, with the extrusion nozzle 55 and housing 70 being fixed.

The control unit 90 includes one or more programmed processors that are adapted to control and vary said rates and speeds depending on a pre-determined input from an operator (not shown). The control unit 90 is further adapted to adjust the respective rates depending on a feedback provided by a sensor 92 adjacently disposed to the extruded compound material 48. The sensor 92 is configured to provide constant feedback to the control unit 90 by measuring the dimension, viscosity or other properties of the extruded compound material 48. By way of example, the sensor 92 can include but not limited, video camera, a laser micrometer, a spectrometer, a thermal imager, or the like, or combinations thereof. The control unit 90 is coupled to, and controls, the parts and features of the assembly 100. The control unit 90 may be remotely coupled (e.g. wired, wireless, or the like) to all the parts and features of the assembly 100.

The freshly deposited compound material 48 on the rotational mandrel 60 has a tightly wound coil-like configuration, where each loop-like or winding bonds to each adjacent loop-like or winding forming the tubular member 20, in view of the properties and temperature of the compound material 48 when extruded. Additionally, a heating member 72 may be disposed adjacent to the extruded compound material 48 on the mandrel 60. The heating member 72 further heats the compound material 48 so that the each loop-like or winding further bonds and fuses to each adjacent loop-like or winding forming the tubular member 20. The heating member 72 is adapted to further assist on the formation of an outer surface 22 of the tubular member 20, so that the outer surface 22 is smoother. The heating member 72 is coupled to the housing 70; the housing 70 may include more than one heating member 72. By way of example, a convective type heating member 72 can have a variety of shapes including but not limited to: elongated plate (FIGS. 2-3), arcuate plate, rectangular, tubular (concentrically disposed around the tubular member 20), or the like, that are adapted to heat the compound material 48. Other types of heating members are anticipated, such as forced convection hot air nozzles and/or RF heaters to selectively heat the mandrel or any ferromagnetic components within the catheter.

Additionally or alternatively to the heating member 72, the outer surface 22 of the tubular member 20 may be coated or laminated with a suitable polymeric material to assist with the smooth property of the outer surface 22. In addition to the heating member 72, a cooling member 74 may be disposed adjacent to the extruded compound material 48 and proximately located from the heating member 72, so that the compound material 48 is cooled after the extrusion. Heating of the mandrel prior to winding of the compound material may also be used to improve bonding to the underlying substrate or substrates that have been previously added on the mandrel to the compound material as it is being wound.

Figure 3:
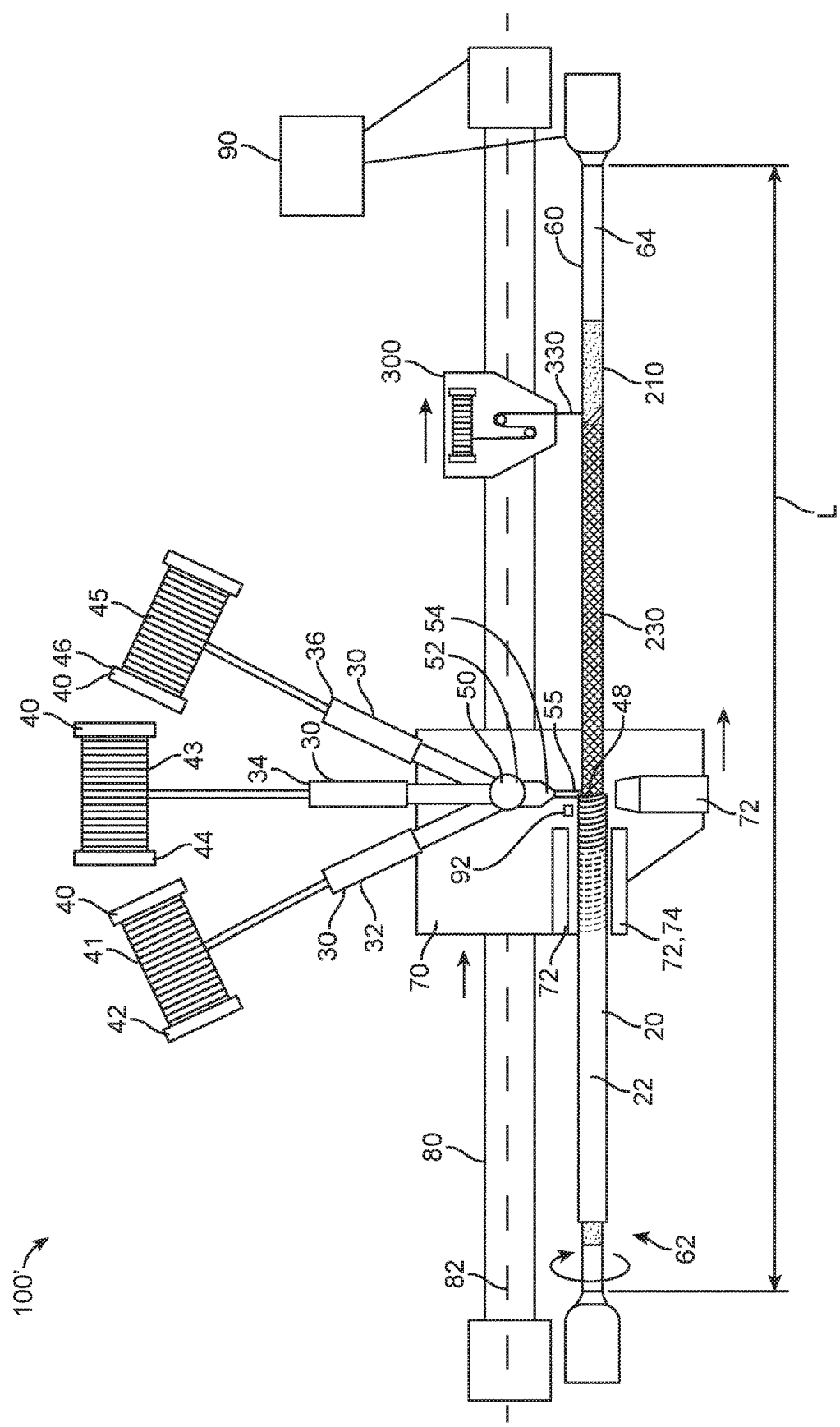
FIG. 3 is a side view of a variable stiffness catheter manufacturing assembly according to an alternative embodiment of the disclosed inventions.

FIG. 3 illustrates an alternative embodiment of the catheter manufacturing assembly 100' constructed in accordance with the disclosed inventions. For ease in illustration and disclosure, the features and configurations of assembly 100' that are the same as assembly 100 of FIG. 2 are given the same reference numerals. The assembly 100' comprises a subassembly 300, slidably coupled to the carrier 80 and distally located from the housing 70. The subassembly 300 is adapted to translate and advance along the longitudinal axis 82 of the carrier 80.

The assembly 100' further includes an inner liner 210 disposed on the catheter formation mandrel 60, as an inner layer of the tubular member 20. The liner 210 is composed of suitable polymeric materials, such as, but not limited to, PTFE, TFE, FEP, HMWPE, HDPE, LDPE, polyimide, PEEK, and combinations thereof. The liner 210 is surrounded by a reinforcement layer 230, such that the reinforcement layer 230 is disposed between the liner 210 and the tubular member 20. The reinforcement layer 230 may be pre-formed on the mandrel or coiled by the subassembly 300, and is composed of suitable metallic and/or polymeric material strand 330, such as stainless steel, Nitinol, CoCr alloys, platinum and Pt alloys, tantalum and Ta alloys, PET, PEEK, aramids, PEN fiber, UHMWPE, PBO, liquid crystalline polymers (e.g., Vectran), carbon fiber and carbon fiber nanomaterial fibers, and combinations thereof. By way of example, the strand 330 may be formed by a core metallic wire having a suitable polymeric coating. The reinforcement layer 230 may be braided or coiled over the liner 210 that is disposed on the catheter formation mandrel 60. The subassembly 300 may be controlled by the control unit 90, or may be controlled by a different control unit in communication with the control unit 90. The control unit 90 may be remotely coupled to the assembly 300, as described above.

Figure 6A:
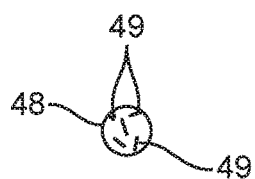
FIGS. 6A-B are cross-sectional views an extruded material according to one embodiment of the disclosed inventions.
Figure 6B:
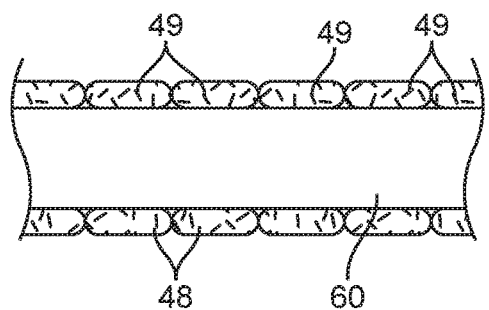

In the embodiment of FIG. 3, the composed material 48 is extruded onto (and covering) the liner 210 and reinforcement layer 230 that are formed and disposed on the catheter formation mandrel 60. The reinforcement layer 230 is adapted to provide further structural support to the tubular member 20. In addition to the reinforcement layer 230 of FIG. 3 or in absence of having said layer 230 (FIG. 2), one or more of the plurality of materials 40 may include filament materials 49, such as, carbon fibers, aramid, Vectran, metals, metals alloys, nano-carbon tubes, tubular or elongate continued fibers, or particles of fiber materials or micro/nanoparticles or the like, or combination thereof, adapted to provide additional structural support to the tubular member 20 when the compound material 48 is extruded (FIGS. 6A-B). The filament materials 49 are configured to align in a field and wrap around in a circumferential orientation when the compound material 48 is extruded, further supporting the structure of the tubular member 20, as depicted in FIG. 6B.

Alternatively, one (or more) of the filaments 41, 43 or 45 of the plurality of materials 40, or additionally to the polymeric filaments 41, 43 and 45 of FIG. 3, a filament may be composed of a material having higher melting point, as previously described, which is adapted to be co-extruded (i.e., through or alongside the nozzle 55) with the compound material 48, as disclosed in FIG. 2.

Figure 4C:
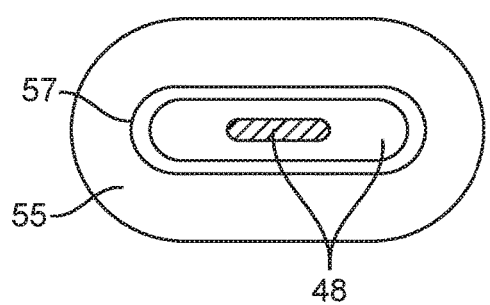

FIGS. 4A-C illustrate extrusion features of the catheter manufacturing assembly 100 constructed in accordance with the disclosed inventions. The compound material 48 is extruded from the nozzle 55 onto the (rotating) catheter formation mandrel 60 to form the tubular member 20. The opening 57 of the extrusion nozzle 55 depicted in FIG. 4B has a circular configuration. Alternatively, the opening 57 of the extrusion nozzle 55 depicted in FIG. 4B has an elliptical/oval configuration, still other opening configurations are anticipated such as square, rectangular or variants with convex or concave edges. The extrusion rate of the compound material 48 out of the nozzle 55 onto the (rotating) catheter formation mandrel 60 is substantially constant, and may be varied depending on a desired thickness of the wall 24 of the tubular member 20. In addition to the rate of extrusion of the compound material 48, the thickness of the wall 24 of the tubular member 20 depends on a variety of factors, such as, the rotational speed of the catheter formation mandrel 60, and/or the translation speed of the extrusion nozzle 55 along length L of the mandrel 60. The higher the extrusion rate of the compound material 48, and/or the rotational speed of the mandrel 60, and/or the linear advancement of the extruded material 48 onto the mandrel 60, the thicker the resultant wall 24. Conversely, the lower the extrusion rate of the compound material 48, and/or rotational speed of the mandrel 60, and/or the linear advancement of the extruded material 48 onto the mandrel 60, the thinner the resultant wall 24. The thickness of the wall 24 may be dynamically varied by the control unit 90, which controls the feed rate of the extruded compound material 48 out of the nozzle 55, the rotational speed of the mandrel 60 and/or the linear advancement speed of the nozzle 55 extruding the compound material 48 onto the mandrel 60.

As described above, the ratio of plurality of materials 40 (i.e., 41, 43 and 45) in the compound material 48 is also dynamically varied by a control unit 90 coupled to the actuators 30, which controls the amount of material each actuator 32, 34 and 36 feeds into the mixer 50 (FIGS. 2-3). So that, the compound material 48 will have different elasticity and strength depending on the ratio of each of the materials mixed into the compound 48; in addition of having a variety of thickness of the wall 24 depending on the above described factors, which may be further controlled by the control unit 90. Further, the temperature of the heating chamber 52 of the mixer 50 may be controlled by the controller 90 to vary as the material ratio and thus the melting point of the blended compound changes to facilitate smooth flow of the compound being extruded.

Additionally, the tubular member 20 manufactured with the assemblies 100 and 100' will have more kink resistance compared to the catheters manufactured with traditional known systems and methods, since most of the property enforcement (i.e., strength) of the tubular member 20 is in the circumferential orientation by extruding the compound material 48 in a coil-like configuration.

Figure 7:
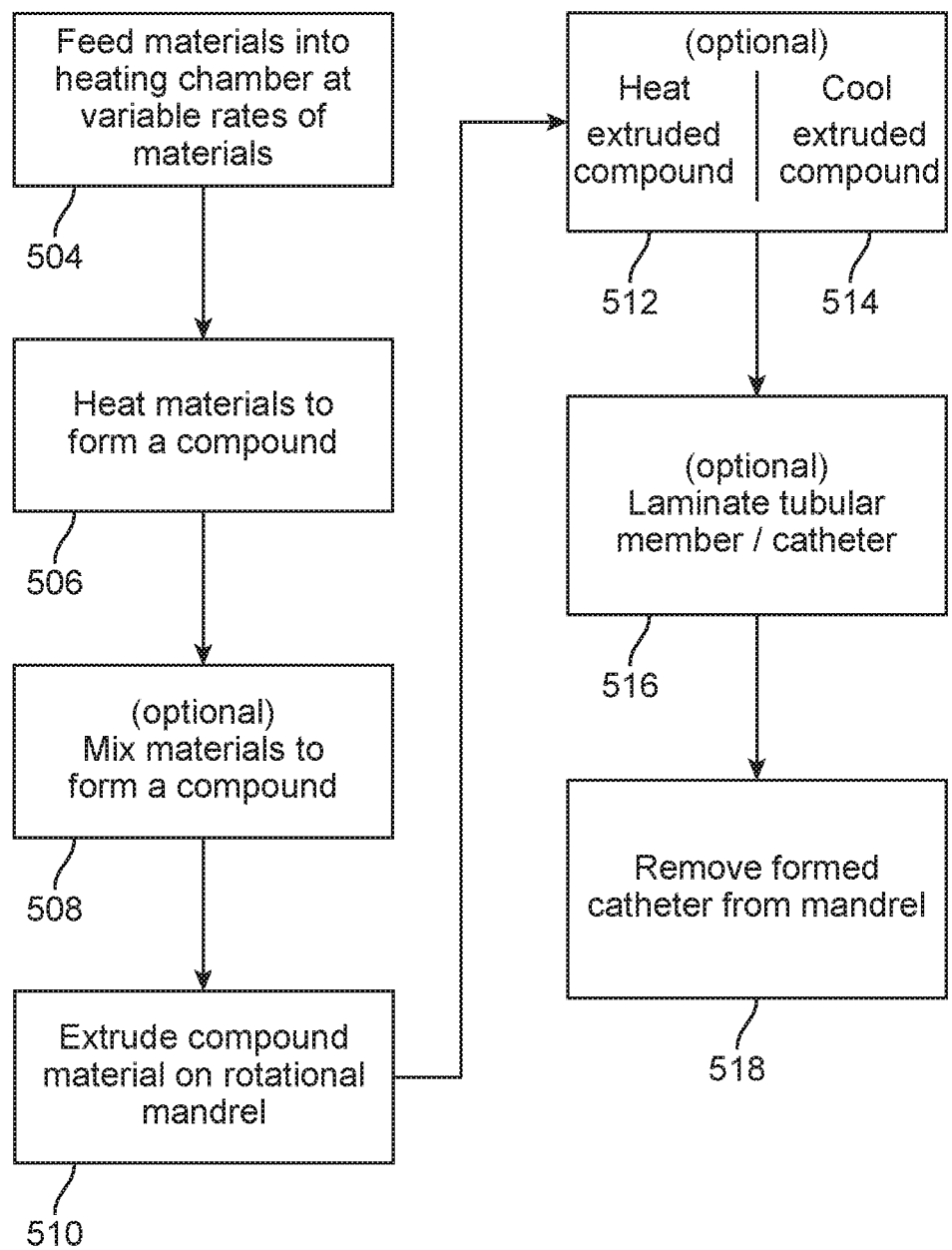
FIG. 7 is a flowchart summarizing the steps in a method of making a variable stiffness catheter according to the embodiments of FIG. 2.

FIG. 7 is a flowchart summarizing the steps in a method of making a variably stiffness catheter according to the embodiment of FIG. 2. At step 504, a plurality of materials 40 are feed into the heating camber 52 of a mixer 50 at a determined rate depending on a desired stiffness of a compound material 48. At step 506, the plurality of materials 40 are heated to a temperature that is dependent on the material ratios to form the compound material 48. At optional step 508, the plurality of materials 40 are further mixed to form the compound material 48. At step 510, the compound material 48 is extruded on a rotating catheter formation 60 while the compound material 48 is also axially moved along the (rotating) mandrel 60, thereby forming the tubular member 20. At optional step 512, the extruded material 48 on the mandrel 60 is heated to further fuse the tubular member 20. At optional step 514, the extruded material 48 on the mandrel 60 is cooled. At optional step 516, the tubular member 20 is laminated with a suitable polymeric material. Lastly at step 518, the fully formed catheter 10 is removed from the mandrel 60.

In alternative embodiments, multiple layers of coil-extruded material may be applied to the catheter mandrel 60 during the catheter formation process. For example, the compound material 48 be extruded onto the mandrel 60 in both directions of axial translation of the housing/nozzle, in which case both leading and trailing heaters may be provided. An advantage of this approach is that no stoppage of the catheter formation process is required between applications of each subsequent material extrusion layer.

Figure 8:
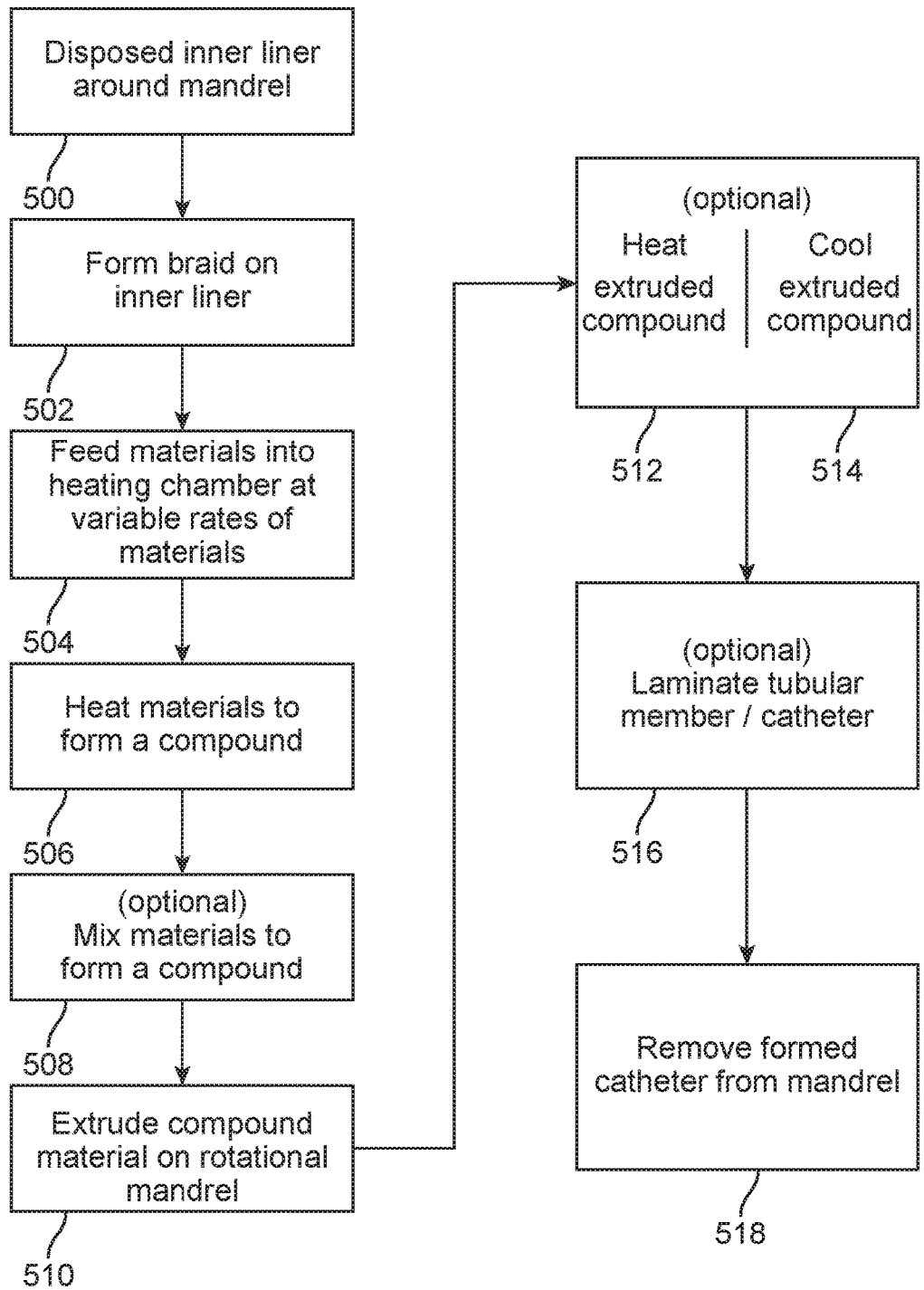
FIG. 8 is a flowchart summarizing the steps in a method of making a variable stiffness catheter according to the embodiments of FIG. 3.

FIG. 8 is a flowchart summarizing the steps in a method of making a variably stiffness catheter according to the embodiment of FIG. 3. At step 500, an inner liner 210 is disposed on/around catheter formation mandrel 60. At step 502, a reinforcement layer 230 is coiled on the inner liner 210 from strand 330. For ease in illustration and disclosure, the steps 504 to 518 are the same as the flowchart of FIG. 7, which are given the same reference numerals.

Accordingly, the disclosed embodiments provide a method of manufacturing catheters that produces a catheter having a variety of properties along its length, such as substantial variations in wall thickness, while having gradual transitions of stiffness, and material layering. The disclosed method allows for large scale production of catheters with a high degree of accuracy and repeatability, and for producing customized variable stiffness catheters, and catheters with higher kink resistance than catheters produced using traditional manufacturing techniques.

While embodiments have been shown and described, various modifications may be made without departing from the scope of the inventive concepts disclosed herein. The invention(s), therefore, should not be limited, except as defined in the following claims.

What is claimed is:

1. A system for manufacturing a catheter, comprising:
   a first material feeder coupled to a first material source;
   a second material feeder coupled to a second material source;
   a thermally controlled mixer coupled to the first and second material feeders, wherein the first material feeder is configured to feed a first material from the first material source into the mixer at a first material feed rate, and the second material feeder is configured to feed a second material from the second material source into the mixer at a second material feed rate, such that the first and second materials are combined in the mixer to form a compound material that varies in content as a function of the respective first and second materials, and of the first and second material feed rates;
   a catheter formation mandrel having a longitudinal axis, the mandrel being controllably rotatable about the longitudinal axis at a mandrel rotation rate;
   an extruder operatively coupled to the mixer and having an output nozzle configured to apply compound material from the mixer onto the catheter formation mandrel; and
   a control system comprising one or more processors that control one or more of the first material feed rate, second material feed rate, and mandrel rotation rate, respectively, so as to enable formation of a catheter having a variable stiffness profile along a length of the catheter,
   wherein the extruder is configured to apply an extrusion of compound material from the mixer onto the catheter formation mandrel such that the extrusion winds around the mandrel forming adjacent loops of compound material on the catheter formation mandrel.

2. The catheter manufacturing system of claim 1, the first and second materials having different elasticity and/or strength characteristics, wherein an elasticity and/or strength of the compound material may be varied by controlling one or both of the first and second material feed rates.

3. The catheter manufacturing system of claim 1, the mixer comprising a heated mixing chamber, wherein the control system controls a temperature of the mixing chamber.

4. The catheter manufacturing system of claim 1, wherein the extruder applies the compound material onto the catheter formation mandrel at a material extrusion rate controlled by the control system independently of the respective first and second material feed rates.

5. The catheter manufacturing system of claim 4, the extruder and/or output nozzle being translatable along the longitudinal axis of the catheter formation mandrel at an extruder translation rate controlled by the control system.

6. The catheter manufacturing system of claim 5, wherein the control system varies a wall thickness along a length of at least a portion of a catheter being formed on the mandrel by varying one or more of the first material feed rate, second material feed rate, mandrel rotation rate, and extruder translation rate.

7. The catheter manufacturing system of claim 5, wherein the control system adjusts one or more of the first material feed rate, second material feed rate, mandrel rotation rate, and extruder translation rate based on real-time measurement data of a diameter of a portion of a catheter being formed on the mandrel.

8. The catheter manufacturing system of claim 5, further comprising two or more heating elements disposed adjacent or otherwise in proximity to a location at which the extruder applies the compound material onto the mandrel, the two or more heating elements comprising
   a first heating element disposed on a first side of the mandrel adjacent or otherwise in proximity to a location at which the extruder applies the compound material onto the mandrel, and
   a second heating element disposed on an opposing side of the mandrel from the first heating element.

9. The catheter manufacturing system of claim 8, wherein the two or more heating elements are coupled to, so as to translate along the mandrel with, the extruder and/or output nozzle.

10. The catheter manufacturing system of claim 1, further comprising a third material feeder coupled to a third material source, wherein the third material feeder is configured to feed a third material from the third material source into the mixer at a third material feed rate controlled by the system controller, such that the first, second and third materials are combined in the mixer to form the compound material, and wherein the compound material varies in content as a function of the respective first, second and third materials, and of the first, second and third material feed rates.

11. The catheter manufacturing system of claim 1, further comprising a third material feeder coupled to a source of material having a higher melting point than said compound material, wherein the third material feeder is configured to feed the material having a higher melting point than said compound material through or alongside the output nozzle with the compound material onto the catheter formation mandrel.

* * * * *